United States Patent [19]

Christensen et al.

[11] Patent Number: 5,116,371
[45] Date of Patent: May 26, 1992

[54] PROSTHESIS WITH IMPROVED BIOCOMPATIBILITY

[76] Inventors: James M. Christensen, 1207 E. Saga, Glendora, Calif. 91740; Parviz R. Ainpour, P.O. Box 70364, Pasadena, Calif. 91117

[21] Appl. No.: 549,096

[22] Filed: Jul. 6, 1990

[51] Int. Cl.$^5$ .............................................. A61F 2/02
[52] U.S. Cl. ............................................ 623/11; 623/8
[58] Field of Search ............................ 623/8, 11, 66

[56] References Cited

U.S. PATENT DOCUMENTS

| | | | |
|---|---|---|---|
| 3,293,663 | 12/1966 | Cronin | 3/36 |
| 4,138,382 | 2/1979 | Polmanteer | 260/29.6 |
| 4,157,085 | 6/1979 | Austad | 128/1 |
| 4,517,326 | 5/1985 | Cordts et al. | 524/310 |
| 4,648,880 | 3/1987 | Brauman | 623/8 |
| 4,731,081 | 3/1988 | Tiffany | 623/8 |
| 4,790,848 | 12/1988 | Cronin | 623/8 |

OTHER PUBLICATIONS

K. Kliment, et al; Use of Spongy Hydron in Plastic Surgery; 1968 J. Biomed. Mater. Res. vol. 2, pp. 237–243.

J. S. Calnan, et al; Clinical and Experimental Studies of Polyhydroxyehtylmethacrylate Gel ("Hydron") for Reconstructive Surgery; British J. Plastic Surg. vol. 24, pp. 113–124.

*Primary Examiner*—David Isabella
*Assistant Examiner*—Gina M. Gualtieri

[57] ABSTRACT

An implantable prosthesis comprises a hydrogel enclosed within a flexible envelope. The hydrogel contains both hydrophilic and hydrophobic domains. It is prepared by copolymerizing a hydrophilic monomer such as water soluble N-vinylpyrrolidone, acrylates or methacrylates with non-water soluble monomers such as acrylates, methacrylates, N-vinyl carbazole, its derivatives, or a non-water soluble derivative of N-vinylpyrrolidone. The flexible envelope may be either porous or non-porous. The hydrogel may be either solid or composed of particles of a size greater than the porosity of the envelope.

16 Claims, No Drawings

PROSTHESIS WITH IMPROVED BIOCOMPATIBILITY

FIELD OF THE INVENTION

The present invention relates to improved implantable prostheses used to reconstruct soft tissue. More specifically, it concerns soft tissue prostheses combining a hydrogel within an envelope in order to minimize capsular formation and contracture.

BACKGROUND OF THE INVENTION

Reconstruction of soft tissues using a silicone elastomer bag filled with silicone gel is a common surgical procedure. Such an implant was described by Cronin in U.S. Pat. No. 3,293,663 for reconstruction of the human breast. However, after a short period of time a capsule composed of fibrous scar tissue forms around the implant. It is commonly believed that silicone gel "bleeding" through the bag causes an inflammatory response which results in this capsular formation. Thickening and eventual contracture of the fibrous capsule results in hardening and spherical deformation of the implant and surrounding tissues. The implant becomes painful, aesthetically unacceptable, and can cause erosion of the overlying tissues.

The use of saline filled silicone elastomer bags and double-lumen implants with the outer chamber containing saline, decreases the inflammatory response. However, failure of the silicone elastomer bag, especially along folds, is more common with saline filled implants. This is due to abrasion of the bag against itself, frequent flexing of the material as the patient moves, the low viscosity of the filling material, and the decreased lubricity of the saline compared to silicone gel. Rupture of a saline filled implant allows the tissue cavity to shrink as the saline is absorbed into the surrounding tissues.

U.S. Pat. No. 4,157,085 to Austad discloses hydrophilic polymers such as poly-N-vinylpyrrolidone, carboxymethylcellulose, or polyethylene glycol encapsulated within a membrane permeable to extracellular body fluids under osmotic pressure. The preferred material is a very thin silicone membrane capable of transmitting fluids as well as stretching as the fluid concentration of the enclosed material increases. This device is intended to be used to stretch tissue as the polymer inside the envelope absorbs fluid. When tissue expansion is completed, the device is removed and replaced with a suitable prosthesis. This is necessary since the polymers inside the envelope are water soluble, not crosslinked, and would readily disperse in the body if they should escape from the device if its membrane ruptured or tore.

Polmanteer in U.S. Pat. No. 4,138,382 discusses the use of hydrophilic gels which are copolymers of olefinic hydrolyzable silanes and water soluble vinylic constituents. These gels swell in the presence of water to form a loose crosslinked network using siloxane [≡Si—O—Si≡] as the covalent crosslinking entity. However, this results in a gel which can dissociate in water according to the equilibrium reaction

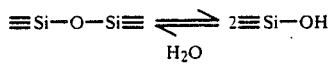

and become soluble. Such gels would slowly be absorbed into the tissue in the event of a rupture or tear in the envelope.

U.S. Pat. No. 4,517,326 to Cordts suggests the use of a polyurethane gel containing an aqueous dispersion for use as an implantable prosthesis. The water level in the gel can only be varied from 25 to 65 percent which limits the softness of the device. Additionally, such a device would contain macroporosity in the form of dispersed water droplets and be susceptible to calcification and tissue ingrowth.

Various medical researchers have evaluated the implantation of poly(hydroxyethyl methacrylate (pHEMA)) as a breast tissue replacement. Depending on the water content, cross-linking agent, monomer content, and pore structure as well as other variables within these implants, a broad range of tissue interaction and encapsulation, small and giant cell growth, vascularization and calcification has been demonstrated. In general, pHEMA hydrogels with high water contents exhibit poorer mechanical properties, tend to calcify, are difficult to shape, and are readily damaged during implantation. This is believed to be due to their macroporous structure at high water contents. Lower water content pHEMA hydrogels which are homogeneous or have only microporosity do not exhibit calcification. However, they are generally stiffer and less malleable and have a greater tendency to incite a fibrous capsule.

The success of post-mastectomy reconstruction, as well as other procedures involving implants of a soft tissue prosthesis, would be greatly enhanced by the use of a prosthesis which is soft and malleable, does not calcify or incite severe fibrous encapsulation, and is resistant to leakage in the event of envelope rupture or tear. The present invention describes such a soft tissue prosthesis containing a less reactive, homogeneous, and more biocompatable filling along with construction designs which provide long term stability even in the event of envelope tear or rupture.

STATEMENT OF THE INVENTION

The present invention is directed to improved implantable prostheses for use in the human body comprising a flexible envelope that contains within it a soft, malleable hydrogel filling containing both hydrophobic and hydrophilic domains. The envelope is formed from either a flexible porous or non-porous material and may be single or multi-lumen.

Percent water content of the hydrogel filling may be varied from 40 to 99 percent and is controlled by the ratio of hydrophobic to hydrophilic domains. These hydrogels are made by copolymerization of a hydrophilic and a hydrophobic monomer. A small amount of multi-functional monomer may also be used as a covalent crosslinker to make the copolymer a thermoset and insoluble in organic media. Even in the absence of a covalent crosslinking monomer, these hydrogels, in an aqueous environment, will remain as a gel due to interaction of the hydrophobic domains. These interactions may be hydrophobic, ionic, dipolar, hydrogen bonding or a combination of these forces. This results in a hydrogel in which the polymer chains are "crosslinked" by the hydrophobic domains. In aqueous, these hydrogels will swell and hold water uniformly in the hydrophilic domains of the polymer without any macroporosity or heterogeneity. This homogeneity reduces or prevents calcification. The hydrophobic domains which are uniformly spread throughout the matrix of the gel hold the polymer chains together and will not allow them to dissolve and dissipate into body fluids.

Examples of hydrophilic monomers that can be used would be any biocompatible, water soluble vinylic constituent. The term "vinylic" is used here to mean that the constituent contains at least one unsatuarated aliphatic linkage in the form of $CH_2=CRR'$. Useful classes of monomers can be N-vinylpyrrolidone, acrylates, or methacrylates having the general formula $$CH_2=\overset{R}{\underset{|}{C}}-CO_2-R'$$

where
  R is H or $CH_3$ and
  R' can be radicals derived from monohydric or dihydric alcohols such as $CH_2-CH_2-OH$ or $CH_2-CH(CH_3)-OH$ or $CH_2-CH(OH)-CH_2-OH$
or monomers having the general formula $$CH_2=\overset{R}{\underset{|}{C}}-CO-\overset{|}{\underset{R'''}{N}}-R''$$

wherein
  R is H or $CH_3$ and
  R'' and R''' can be H, alkyls, or alkane derived radicals such as $CH_3$, $C_2H_5$, or monohydric alcohols such as $CH_2-CH(OH)-CH_3$ Other vinylic constituents containing 2 or more vinylic groups can be used to modify the properties of the gel in order to adjust the swelling, solubility, flexibility, and cohesiveness.

Examples of hydrophobic monomers that can be used are any suitable biocompatible, hydrophobic vinylic constituent. Useful classes of monomers can be acrylates, methacrylates, and $RR'-N-CH_2=CH_2$ that are hydrophobic.

Examples include monomers having the following general formula $$CH_2=\overset{R}{\underset{|}{C}}-CO_2R'$$

where
  R is H or $CH_3$ and
  R' is $CH_3$, $CH_2-CH_3$ or higher alkyls; alternatively, R' may be benzyl, phenyl, or other suitable aromatic groups.

Other monomers can be non-water soluble derivatives of N-vinylpyrrolidone, or aromatic derivatives of N-vinylpyrrolidone such as N-vinyl carbazole. The term aromatic derivatives of N-vinylpyrrolidone is meant to include N-vinylpyrrolidone with one or more aromatic rings attached thereto. These derivatives may also include the addition of pendant groups such as oxygen, halogen, or alkyls.

Other classes of hydrogels having both hydrophobic and hydrophilic domains include polyurethanes containing a hydrophilic polyol domain and a hydrophilic alky or aryl di-isocyanate. Similarly, hydrolyzed polyacrylonitriles contain carboxylic acid or amide groups, that form the hydrophilic domains, and nitrile $[-C\equiv N]$ groups that interact strongly to form the hydrophobic domains.

The envelope containing the hydrogel may be formed from any suitable material that is flexible and biocompatible. Non-porous materials such as silicone or polyurethane having either a smooth or textured surface may be used. Porous materials made from fabricated polymers which are woven, knitted, felted, or veloured, or materials which are foamed, stretched, or expanded may also be used. The pore size of these materials should be less than the smallest particle size of hydrogel used to fill the prosthesis in order to avoid loss of hydrogel from the envelope. Permeable membranes such as thin cellulosic or silicone may also be used.

EXAMPLE 1

A single walled silicone elastomer bag is filled with hydrogel then sealed to provide a barrier to fluid and tissue exchange. The hydrogel inside the bag is a solid mass preferably having a shape similar to the desired natural contour of the body. Such a hydrogel would preferably have a high water content around 95 to 99 percent in order to provide the desired softness to the implant. However, a lower water content hydrogel could be used if a stiffer implant was desired.

Likewise, the hydrogel inside the bag could be composed of many pieces ranging from chunks down to very small particles. The water content of the hydrogel would depend on the size of the particle and the desired softness of the implant. Large particle sizes would preferably use high water content hydrogels around 95 to 99 percent, similar to the solid mass described above. Smaller particle sizes could use lower water content hydrogels down to 40% to achieve the same effect due to the fluidity of the particles. If higher water content hydrogels were used with small particles a more "gelatinous" type structure would be obtained.

EXAMPLE 2

A single walled bag formed from a porous material is filled with hydrogel then closed to prevent escape of the hydrogel. Suitable materials for the bag would be biocompatible, would not elicit a severe foreign body response, and would have a pore size less than the particle size of the hydrogel. Preferred material would be fabrics made from Teflon, Dacron, or other biocompatible polymers which may be woven, knitted, braided, or formed into felt, or velour. Other preferred materials would include permeable membranes or expanded material such as Teflon which are made porous by stretching. Such a material is sold commercially under the name Goretex.

As in Example 1 discussed above, the hydrogel inside the porous bag could be of several forms and water contents depending on the desired natural curvature and stiffness desired. In this example body fluids are able to transport through the porous bag so that the fluid content inside the bag will stay in equilibrium with the surrounding tissue. However, the components of the hydrogel are retained within the envelope. Tissue ingrowth, if desired, is regulated by the envelope construction and pore size.

EXAMPLE 3

A double lumen implant can be constructed from a bag within a bag. The inner wall and contents of the inner bag can be formed from any materials known to the art. This would include for example silicone gel contained within a silicone elastomer bag. The inner lumen can also be formed according to the present invention as discussed in Examples 1 and 2 above.

The outer lumen is formed with hydrogel surrounding the inner wall and contained within the outer bag. The hydrogel and flexible outer bag can be formed as described in Examples 1 and 2 above.

EXAMPLE 4

A multiple lumen implant can be formed similar to that described in Example 3. For a multiple lumen implant all of the inner walls can be formed with any material known to the art or emcompassed in the present invention. The outer wall or walls are formed according to the present invention as discussed in Examples 1 and 2.

Although the invention has been described above with respect to certain of its preferred embodiments it will be understood that the invention is subject to variations and obvious modifications without departing from its intended scope. Thus, for example, in addition to mammary prosthesis the improved implantable devices of this invention can also be prepared in different shapes and forms for the purpose of supplementing, augmenting or replacing tissue anywhere on or in the animal or human body for aesthetic, reconstructive medical purposes. Augmentation of tissue include augmentation of hypoplastic or missing tissue for reconstructive purposes.

What is claimed is:

1. A surgically implantable prosthesis comprising at least an outer flexible envelope having enclosed therein a hydrogel having both hydrophobic and hydrophilic regions wherein the improvement consists of hydrophobic regions selected from the group consisting of polymerized N-vinylic hydrophobic monomers, hydrolyzed polyacrylonitriles, and combinations thereof.

2. The prosthesis of claim 1 wherein the hydrophobic regions of the hydrogel are held together with hydrophobic, ionic, dipolar, hydrogen bonding or a combination of these forces.

3. The prosthesis of claim 1 wherein at least the outer envelope is constructed of a non-porous material.

4. The prosthesis of claim 3 wherein the hydrogel filling is a blend of hydrogel particles dispersed in a liquid carrier.

5. The prosthesis of claim 1 wherein at least the outer envelope is constructed of a porous or semi-permeable material.

6. The prosthesis of claim 5 wherein the porosity of the outer envelope is designed to allow fluid interchange without large molecule or cellular infiltration.

7. The prosthesis of claim 5 wherein the outer envelope is designed to allow a controlled amount of tissue ingrowth and capsule formation.

8. The prosthesis of claim 5 wherein the outer envelope is constructed of a woven, knitted, felted, veloured, or foamed fabric.

9. The prosthesis of claim 5 wherein the outer envelope is constructed of a stretched or expanded material to create porosity or permeability.

10. The prosthesis of claim 1 further comprising an inner envelope enclosed within the outer envelope wherein at least the space between the inner and outer envelopes is filled with the hydrogel.

11. The prosthesis of claim 5 wherein the hydrogel filling is composed of particles having a size larger than the porosity of the outer envelope.

12. The prosthesis of claim 1 wherein the hydrogel is prepared by the copolymerization of a hydrophilic monomer with a N-vinylic hydrophobic monomer.

13. The prosthesis of claim 1 for use in augmenting or replacing breast tissue.

14. A surgically implantable prosthesis comprising at least an outer flexible envelope having enclosed therein a hydrogel having both hydrophobic and hydrophilic regions wherein the hydrogel is prepared by the copolymerization of a hydrophilic monomer with a N-vinylic hydrophobic monomer.

15. The prosthesis of claim 14 wherein the hydrophilic monomer is a water soluble vinylic compound of the formula

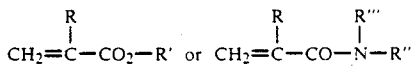

wherein
R is H or $CH_3$,
R' is $CH_2-CH_2-OH$, $CH_2-CH(CH_3)-OH$, or $CH_3-CH(OH)-CH_2-OH$ and
R" and R'" are H, $CH_3$, $C_2H_5$, or $CH_2-CH(OH)-CH_3$
and the hydrophobic monomer is a non-water soluble compound of the formula

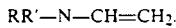

where R or R' are hydrophobic compounds selected from the group consisting of N-vinylcarbazole, its derivatives, non-water soluble derivatives of N-vinylpyrrolidone, aromatic derivatives of N-vinylpyrrolidone, N-vinylcarbazole, and their derivatives.

16. A surgically implantable prosthesis comprising at least one flexible envelope having enclosed therein a hydrogel wherein the hydrogel comprises a hydrolyzed polyacrylonitrile having both carboxylic or amide groups and nitrile groups.

* * * * *